United States Patent
Ding et al.

(10) Patent No.: US 10,127,665 B1
(45) Date of Patent: Nov. 13, 2018

(54) INTELLIGENT ASSISTANT JUDGMENT SYSTEM FOR IMAGES OF CERVIX UTERI AND PROCESSING METHOD THEREOF

(71) Applicants: Hefei University of Technology, Hefei, Anhui (CN); Hefei DVL Electron Co., Ltd, Hefei, Anhui (CN)

(72) Inventors: Shuai Ding, Anhui (CN); Shanlin Yang, Anhui (CN); Weidong Zhao, Anhui (CN); Jie Ma, Anhui (CN); Qiang Fu, Anhui (CN); Lin Zhang, Anhui (CN); Zeyuan Wang, Anhui (CN)

( * ) Notice: Subject to any disclaimer, the term of this patent is extended or adjusted under 35 U.S.C. 154(b) by 0 days.

(21) Appl. No.: 15/975,725

(22) Filed: May 9, 2018

(30) Foreign Application Priority Data

Jul. 31, 2017 (CN) .......................... 2017 1 0642446

(51) Int. Cl.
| | |
|---|---|
| G06T 7/00 | (2017.01) |
| G16H 30/20 | (2018.01) |
| G16H 50/20 | (2018.01) |
| A61B 1/00 | (2006.01) |
| A61B 1/045 | (2006.01) |
| A61B 1/06 | (2006.01) |
| A61B 1/303 | (2006.01) |
| A61B 5/00 | (2006.01) |

(52) U.S. Cl.
CPC ........ *G06T 7/0014* (2013.01); *A61B 1/00006* (2013.01); *A61B 1/045* (2013.01); *A61B 1/0661* (2013.01); *A61B 1/303* (2013.01); *A61B 5/0084* (2013.01); *A61B 5/4331* (2013.01); *A61B 5/7264* (2013.01); *G16H 30/20* (2018.01); *G16H 50/20* (2018.01); *G06T 2207/10068* (2013.01); *G06T 2207/30096* (2013.01)

(58) Field of Classification Search
CPC ......... G06T 7/0014; G06T 2207/10068; G06T 2207/30096; G16H 30/20; G16H 50/20; A61B 1/00006; A61B 1/045; A61B 1/0661; A61B 1/303; A61B 5/0084; A61B 5/4331; A61B 5/7264
See application file for complete search history.

(56) References Cited

U.S. PATENT DOCUMENTS

2016/0328845 A1    11/2016   Seth et al.

FOREIGN PATENT DOCUMENTS

| CN | 105512473 | 4/2016 |
| CN | 105520712 | 4/2016 |

*Primary Examiner* — Michael Rozanski
(74) *Attorney, Agent, or Firm* — Wayne & Ken, LLC; Tony Hom

(57) ABSTRACT

The present invention discloses an intelligent assistant judgment system for images of cervix uteri and a processing method thereof. This system comprises a colposcope device and an assistant judgment device. By combining the colposcope device and the assistant judgment device together to obtain the images of the cervix uteri to be detected by the colposcope device and to compare and analyze the images of the cervix uteri to be detected and its characteristic data by the assistant judgment device, the present invention can judge whether the current cervix uteri to be detected are normal cervix uteri, and can obtain, from the characteristic data of the images of the cervix uteri to be detected, the type of a lesion occurring in the current cervix uteri to be detected and characteristic parameters of the lesion. The doctors are assisted in making correct diagnosis and judgment.

8 Claims, 9 Drawing Sheets

(1)

INTELLIGENT ASSISTANT JUDGMENT SYSTEM FOR IMAGES OF CERVIX UTERI AND PROCESSING METHOD THEREOF

TECHNICAL FIELD

The present invention relates to the technical field of medical devices, and in particular an intelligent assistant judgment system for images of cervix uteri and a processing method thereof.

BACKGROUND OF THE PRESENT INVENTION

Cervical cancer is the only cancer with definite nosogenesis in all human cancers and also the only cancer that can be reduced or eliminated through human prevention. Cervical erosion, cervical polyps, cervical intraepithelial neoplasia, cervical cancer, vaginitis, vulvar, vaginal or cervical neoplasia, virus infections, and subclinical papillomavirus infections can be detected through a colposcope. The colposcope has an application value in diagnosing early cervical canceration and distinguishing tumors from inflammation, and also has a special application value in the treatment of cervical epithelial neoplasia. Because the location and range of the cervical epithelial lesions can be determined through the colposcope, the acquisition and storage of video images of the colposcope or a computer are important for tracking cervical lesions.

In the prior art, in use of the colposcope, doctors, based on images acquired by the colposcope, make judgment and evaluation on the images acquired by the colposcope by observing changes of cervical epithelium by naked eye after the use of physiological saline, 5% acetic acid solution and 5% compound iodine solution. However, there are insufficient gynecologists who know about the colposcope and diagnosis currently. At the same time, there are no standardized diagnostic criteria in the examination of cervical cancer. Therefore, it is impossible to ensure the correct examination operation of the grassroots medical staff. Incorrect image analysis can lead to error biopsy of abnormal parts, thus resulting in misdiagnosis, missed diagnosis or excessive biopsy. In addition, since there are no quantitative standards and unified evaluation standards, different experts will have different evaluation results (subject to subjective factors) on images of the same patient even if the experts are gathered to evaluate the examined and collected images. This affects the accuracy and consistency of evaluation.

Based on the above technical problems, an intelligent identification method for images from a colposcope is provided in Chinese patent application CN201510870263.2, which improves the screening speed by only extracting characteristics of images of a suspected lesion area, and improves the diagnosis consistency of the different doctors on the same image to some extent through a computer assisted diagnosis technology and comparison of standard colposcope image library on the same screen. Although the above invention solves the problems in the existing cervical cancer diagnosis process to some extent, there are certain errors occurred in the judgment due to comparison only on the lesion areas. Moreover, the diagnosis is made only against patients suffering from the cervical cancer, which is not applicable to routine examinations of the cervix uteri.

SUMMARY OF THE PRESENT INVENTION

The invention provides an intelligent assistant judgment system for images of cervix uteri and a processing method with wide range of application, convenient usage and more accurate judgment, so as to solve the problems of inaccurate diagnosis and narrow range of application of existing diagnosis devices for cervix uteri.

In one aspect, the present invention provides an intelligent assistant judgment system for images of cervix uteri, including a colposcope device used for acquiring images of cervix uteri and collecting characteristic data of the images of the cervix uteri; and an assistant judgment device communicated with the colposcope device, the assistant judgment device including a processing unit, a storage module and a comparison and analysis module, and the storage module and the comparison and analysis module being electrically connected to the processing unit respectively, wherein the storage module is provided with a preliminary screening model and a plurality of characteristic models therein, wherein a plurality of different preliminary screening case models which consist of images of diseased cervical uteri and a plurality of different preliminary screening normal models which consist of images of normal cervical uteri are arranged in the preliminary screening model, and the characteristic models correspond to the preliminary screening case models.

The characteristic models consist of a plurality of different diseased characteristic sub-models, and the characteristic sub-models include lesions type names corresponding to the sub-models, characteristic parameters of lesion areas, and characteristic images of the lesion areas.

Based on the above solution, preferably, the comparison and analysis module includes a pixel analysis module and a data analysis module, and the pixel analysis module is configured to carry out pixel comparison and analysis on the images of the cervix uteri to be detected and the preliminary screening model in the storage module to obtain the preliminary screening case models corresponding to the images of the cervix uteri to be detected; and the data analysis module is configured to carry out pixel comparison and analysis on the images of the cervix uteri to be detected and the characteristic models to find characteristic sub-models which are similar to image data of the cervix uteri to be detected.

Based on the above solution, preferably, the assistant judgment device further includes a display unit electrically connected to the processing unit.

Based on the above solution, preferably, the images of the cervix uteri include six state diagrams, including a white light state diagram formed when the cervix uteri are exposed to white light, a green light state diagram formed when the cervix uteri are exposed to green light, an acetic acid state diagram formed when the cervix uteri are exposed to acetic acid for 60 seconds, an acetic acid state sub-diagram formed when the cervix uteri are exposed to acetic acid for 90 seconds, a secondary acetic acid state diagram formed when the cervix uteri are exposed to acetic acid for 120 seconds and an iodine-stained state diagram formed when the cervix uteri are stained with iodine.

Based on the above solution, preferably, each of the preliminary screening case models and each of the preliminary screening normal models consist of images of the cervix uteri in the six different states, and the characteristic images of the lesion areas in the characteristic sub-models include six different state images.

Based on the above solution, preferably, the colposcope device includes a main colposcope, a controller, an imaging probe, a lighting source and an imaging camera; the lighting source, the controller and the imaging camera are mounted on the main colposcope, and the lighting source, the imaging probe and the lighting source are electrically connected to the controller.

The present invention further provides a method for processing the intelligent assistant judgment system for images of cervix uteri, including:

a step A1 of analyzing images of cervix uteri to be detected and a preliminary screening model based on the images of the cervix uteri to be detected and characteristic data of the images of the cervix uteri to be detected so as to determine characteristic models which are similar to the images of the cervix uteri to be detected; and a step A2 of comparing image characteristic data of the images of the cervix uteri to be detected with characteristic sub-models to obtain the characteristic sub-models corresponding to the images of the cervix uteri to be detected, wherein a plurality of different preliminary screening case models which consist of images of diseased cervical uteri and a plurality of different preliminary screening normal models which consist of images of normal cervical uteri are arranged in the preliminary screening model, and the characteristic models correspond to the preliminary screening case models; and the characteristic models consist of a plurality of different diseased characteristic sub-models, and the characteristic sub-models include lesions type names corresponding to the characteristic sub-models, characteristic parameters of lesion areas, and characteristic images of the lesion areas.

Based on the above solution, preferably, the images of the cervix uteri to be detected in the step A1 are acquired by a colposcope device.

Based on the above solution, preferably, the step A2 includes the following steps in detail:

a step A21 of analyzing the images of the cervix uteri to be detected and the preliminary screening model to determine preliminary screening case models which are similar to the images of the cervix uteri to be detected; and a step A22 of acquiring characteristic models corresponding to the images of the cervix uteri to be detected based on the correspondence between the preliminary screening case models and the characteristic models.

The present invention provides an intelligent assistant judgment system for images of cervix uteri. By combining the colposcope device and the assistant judgment device together to obtain the images of the cervix uteri to be detected and its characteristic data by the colposcope device and to compare and analyze the images of the cervix uteri to be detected and its characteristic data by the assistant judgment device, the present invention can judge whether the current cervix uteri to be detected are normal cervix uteri, and can obtain, from the characteristic data of the images of the cervix uteri to be detected, the type of a lesion occurring in the current cervix uteri to be detected and characteristic parameters of the lesion. The doctors are assisted in making correct diagnosis and judgment. This improves the diagnostic level of the doctors and reduces the probability of misdiagnosis and missed diagnosis.

DETAILED DESCRIPTION OF THE PRESENT INVENTION

The specific embodiments of the present invention will be further described in detail with reference to the drawings by the embodiments. The following embodiments are used for describing the present invention, but not for limiting the scope thereof.

Figure 1:
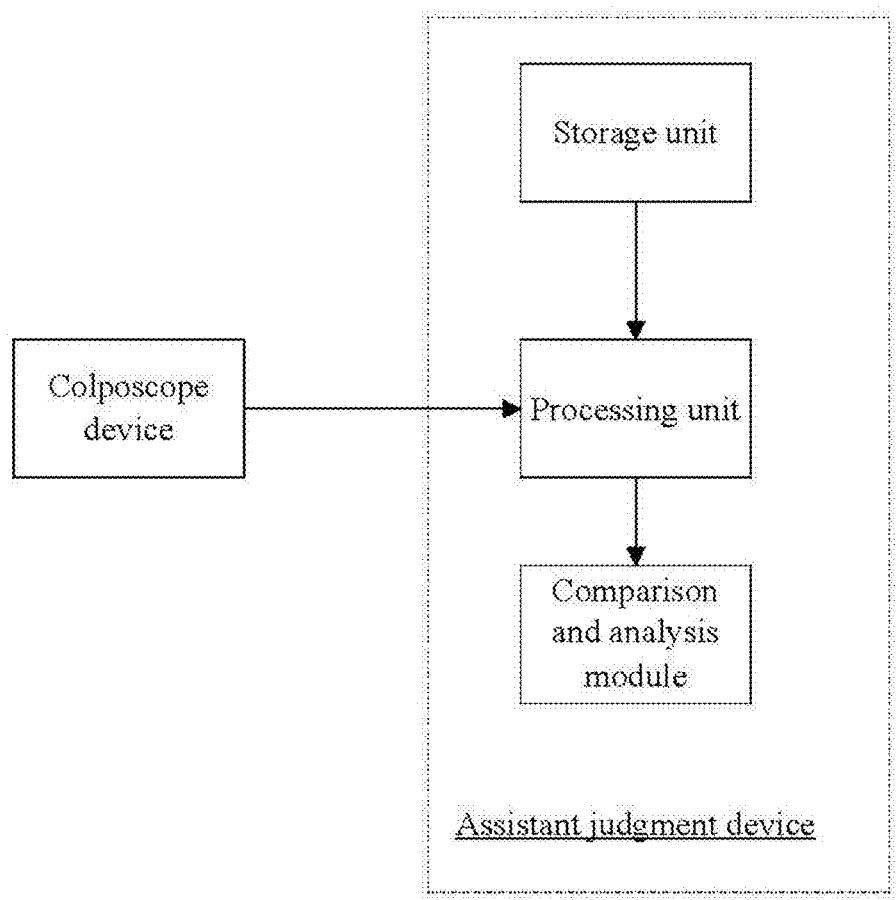
FIG. 1 is a structural block diagram of an intelligent assistant judgment system for images of cervix uteri according to the present invention.
Figure 2:
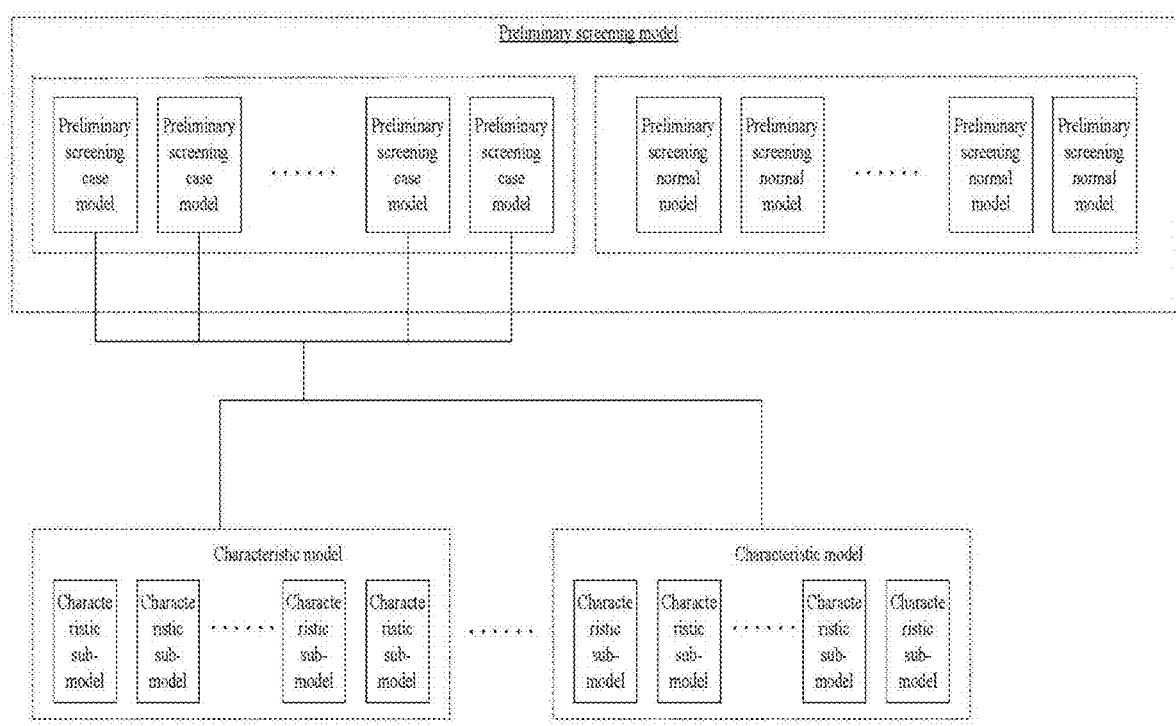
FIG. 2 is a structural block diagram of preliminary screening models and characteristic models in a storage unit according to the present invention.

With reference to FIGS. 1 and 2, the present invention provides an intelligent assistant judgment system for images of cervix uteri, including:

a colposcope device used for acquiring images of cervix uteri and collecting characteristic data of the images of the cervix uteri; and an assistant judgment device communicated with the colposcope device to obtain the images of the cervix uteri to be detected and its characteristic data acquired by the colposcope device.

According to the present invention, the assistant judgment device includes a processing unit, a storage module and a comparison and analysis module, and the storage module and the comparison and analysis module are electrically connected to the processing unit respectively.

According to the present invention, the storage module is provided with a preliminary screening model and a plurality of characteristic models therein, wherein a plurality of different preliminary screening case models which consist of images of diseased cervical uteri and a plurality of different preliminary screening normal models which consist of images of normal cervical uteri are arranged in the preliminary screening model, and the characteristic models correspond to the preliminary screening case models.

According to the present invention, the characteristic models consist of a plurality of different diseased characteristic sub-models, and the characteristic sub-models include lesions type names corresponding to the characteristic sub-models, characteristic parameters of lesion areas, and characteristic images of the lesion areas.

When used, the colposcope device is used for acquiring the images of the cervix uteri to be detected and its characteristic data, and then sending the images to the assistant judgment device.

The assistant judgment device reads preliminary screening model data from the storage module through the processing unit, and controls the comparison and analysis module to carry out image pixel analysis on the images of the cervix uteri to be detected and the primary screening models to determine whether the images of the cervix uteri to be detected belong to the preliminary screening normal model or the preliminary screening case model; if the cervix uteri to be detected belong to the preliminary screening normal model, the processing module shows that the current cervix uteri to be detected are in a normal state, thereby realizing the purpose of the preliminary screening.

If the comparison and analysis module analyzes the images to obtain a result that the current cervix uteri to be detected correspond to a certain primary screening case models in the primary screening models, it shows that such cervix uteri to be detected are diseased cervix uteri. At this moment, in order to further determine detailed information of the cervix uteri, the comparison and analysis module in the present invention also compares and analyzes the cervix uteri and corresponding characteristic models to obtain characteristic sub-models which are similar to the detected cervix uteri so as to determine the information of the diseased cervix uteri and assist the doctors in making the judgment.

In another embodiment of the present invention, the comparison and analysis module in the present invention includes a pixel analysis module and a data analysis module, wherein the pixel analysis module is configured to carry out pixel comparison and analysis on the images of the cervix uteri to be detected and the preliminary screening model in the storage module to obtain the preliminary screening case models corresponding to the images of the cervix uteri to be detected.

The data analysis module is configured to carry out pixel comparison and analysis on the images of the cervix uteri to be detected and the characteristic models to find characteristic sub-models which are similar to image data of the cervix uteri to be detected.

Further, the assistant judgment device in the present invention further includes a display unit electrically connected to the processing unit. When the comparison and analysis module acquires information about test results of the current cervix uteri to be detected, it will send the information to the display unit through the processing unit for display, so that the doctors can intuitively understand the test results of the current cervix uteri to assist the judgment.

In order to ensure the accuracy of the assistant judgment device in the present invention, the images of the cervix uteri include six state diagrams as shown in FIG. 4, FIG. 5, FIG. 6, FIG. 7, FIG. 8 and FIG. 9. The six state diagrams includes a white light state diagram formed when the cervix uteri are exposed to white light, a green light state diagram formed when the cervix uteri are exposed to green light, an acetic acid state diagram formed when the cervix uteri are exposed to acetic acid for 60 seconds, an acetic acid state sub-diagram formed when the cervix uteri are exposed to acetic acid for 90 seconds, a secondary acetic acid state diagram formed when the cervix uteri are exposed to acetic acid for 120 seconds and an iodine-stained state diagram formed when the cervix uteri are stained with iodine.

Further, according to present invention, each of the preliminary screening case models and each of the preliminary screening normal models consist of images of the cervix uteri in the six different states, and the characteristic images of the lesion areas in the characteristic sub-models include characteristic images of six different state images.

The images of the cervix uteri in the six different states of the preliminary screening normal models include a white light state diagram formed when the normal cervix uteri are exposed to white light, a green light state diagram formed when the normal cervix uteri are exposed to green light, an acetic acid state diagram formed when the normal cervix uteri are exposed to acetic acid for 60 seconds, an acetic acid state sub-diagram formed when the normal cervix uteri are exposed to acetic acid for 90 seconds, a secondary acetic acid state diagram formed when the normal cervix uteri are exposed to acetic acid for 120 seconds and an iodine-stained state diagram formed when the normal cervix uteri are stained with iodine, respectively.

According to the present invention, the images of the cervix uteri in the six different states of the preliminary screening case models include a white light state diagram formed when the diseased cervix uteri are exposed to white light, a green light state diagram formed when the diseased cervix uteri are exposed to green light, an acetic acid state diagram formed when the diseased cervix uteri are exposed to acetic acid for 60 seconds, an acetic acid state sub-diagram formed when the diseased cervix uteri are exposed to acetic acid for 90 seconds, a secondary acetic acid state diagram formed when the diseased cervix uteri are exposed to acetic acid for 120 seconds and an iodine-stained state diagram formed when the diseased cervix uteri are stained with iodine, respectively.

When used, the colposcope device acquires the images of the cervix uteri to be detected in the six different states, and then compares the images with the primary screening models and the characteristic models respectively, and the images of the cervix uteri in the six different states in the primary screening models and the characteristic models are used for comparing with each image in a one-to-one correspondence manner. In comparison, the images are judged to be similar only when the six images are all similar to improve the accuracy of the judgment.

With continued reference to FIG. 1 to further describe the technical solution of the present invention, the colposcope device in the present invention includes a main colposcope, a controller, an imaging probe, a lighting source and an imaging camera; the lighting source, the controller and the imaging camera are mounted on the main colposcope, and the lighting source, the imaging probe and the lighting source are electrically connected to the controller. During acquisition of the images of the cervix uteri and the data, the imaging probe acquires imaging data by irradiating the cervix uteri by white light and green light emitted from the lighting source, and sends the imaging data to the controller which sends the data to the assistant judgment device.

Figure 3:
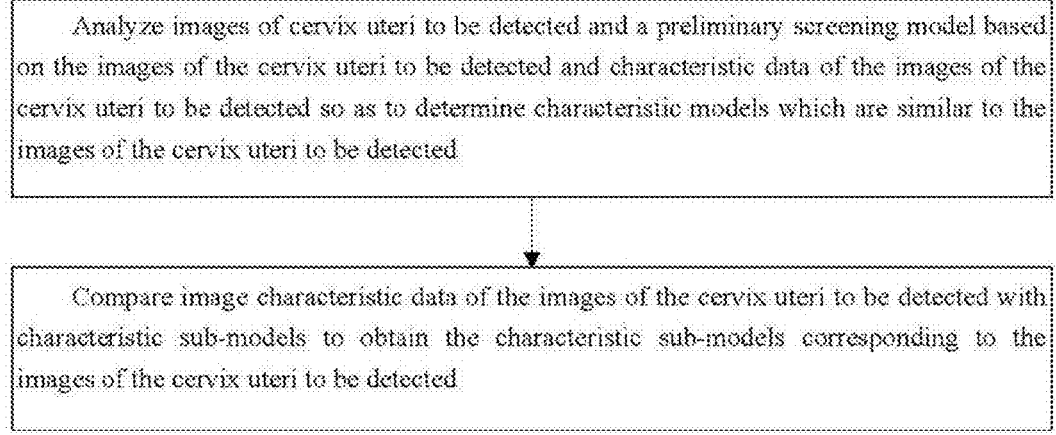
FIG. 3 is a flowchart of a method for processing the intelligent assistant judgment system for images of cervix uteri according to the present invention.
Figure 4:
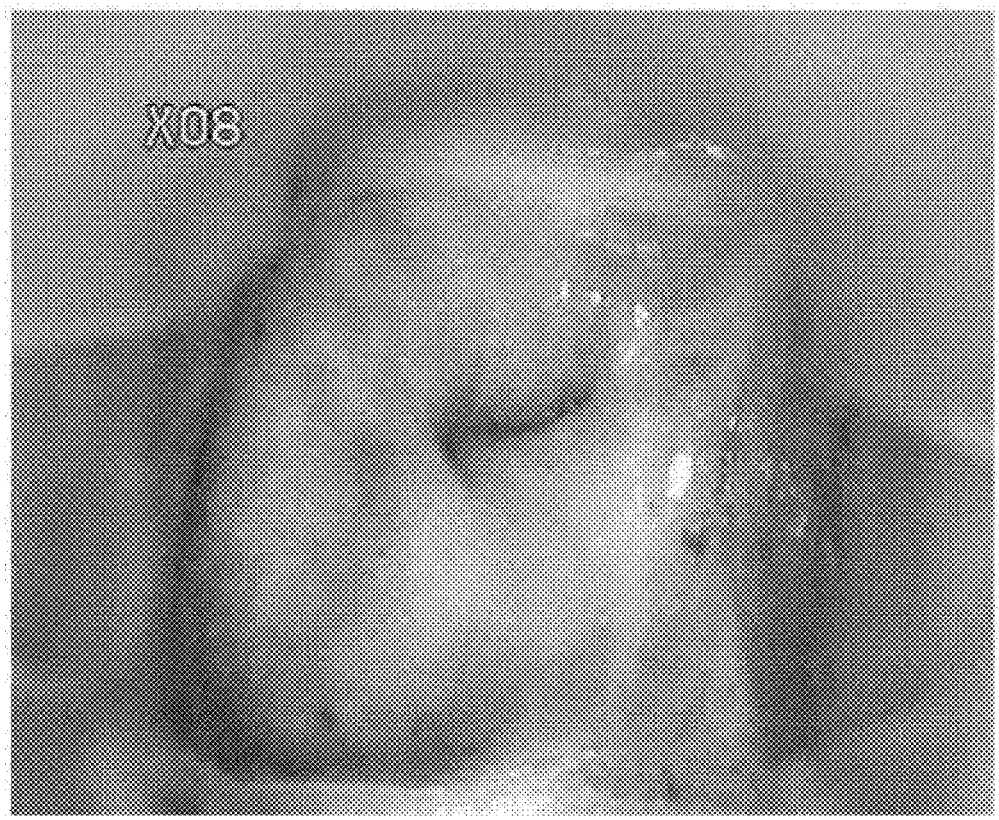
FIG. 4 is a white light state diagram formed when the cervix uteri are exposed to white light according to the present invention.
Figure 5:
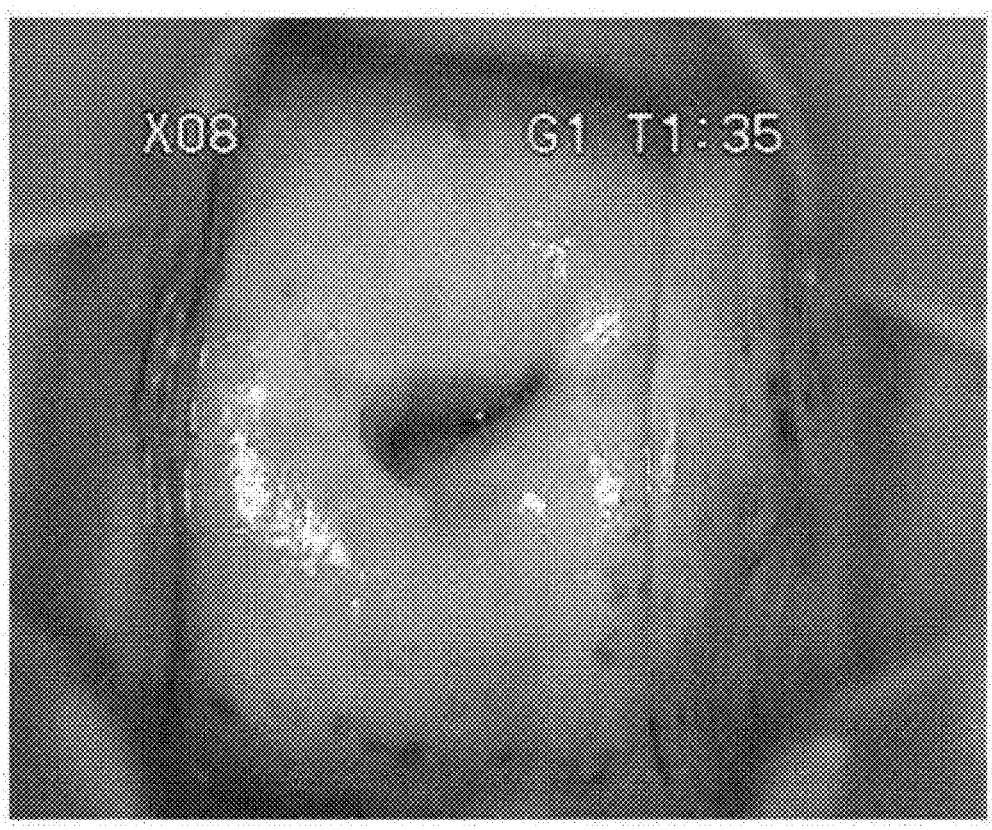
FIG. 5 is a green light state diagram formed when the cervix uteri are exposed to green light according to the present invention.
Figure 6:
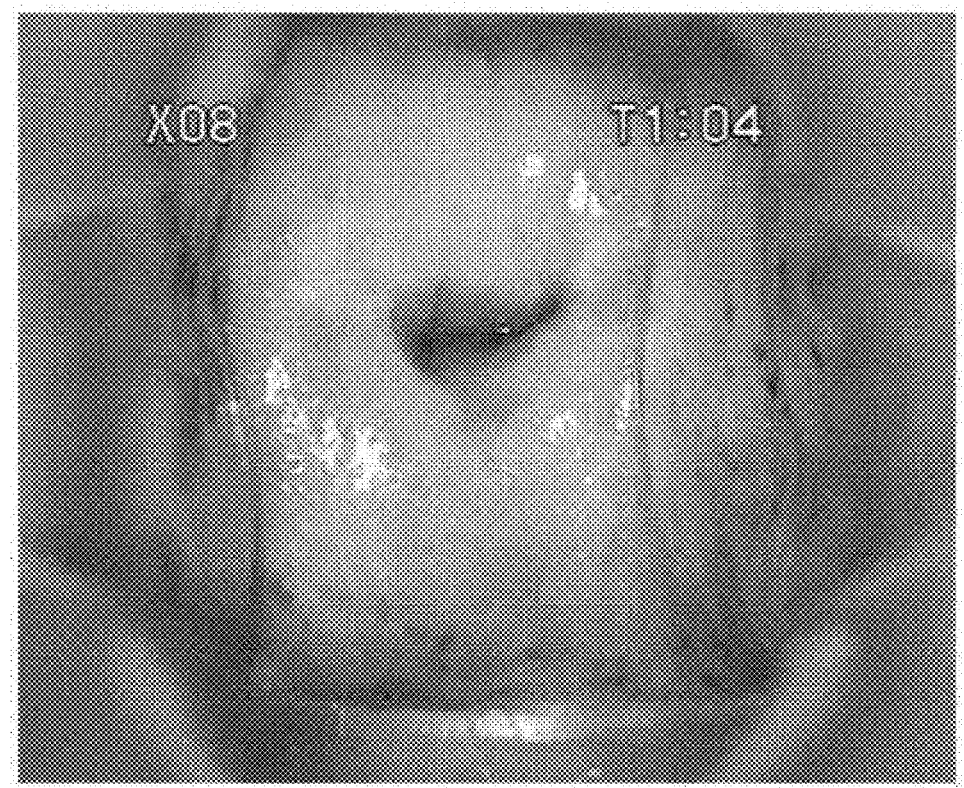
FIG. 6 is an acetic acid state diagram formed when the cervix uteri are exposed to acetic acid for 60 seconds according to the present invention.
Figure 7:
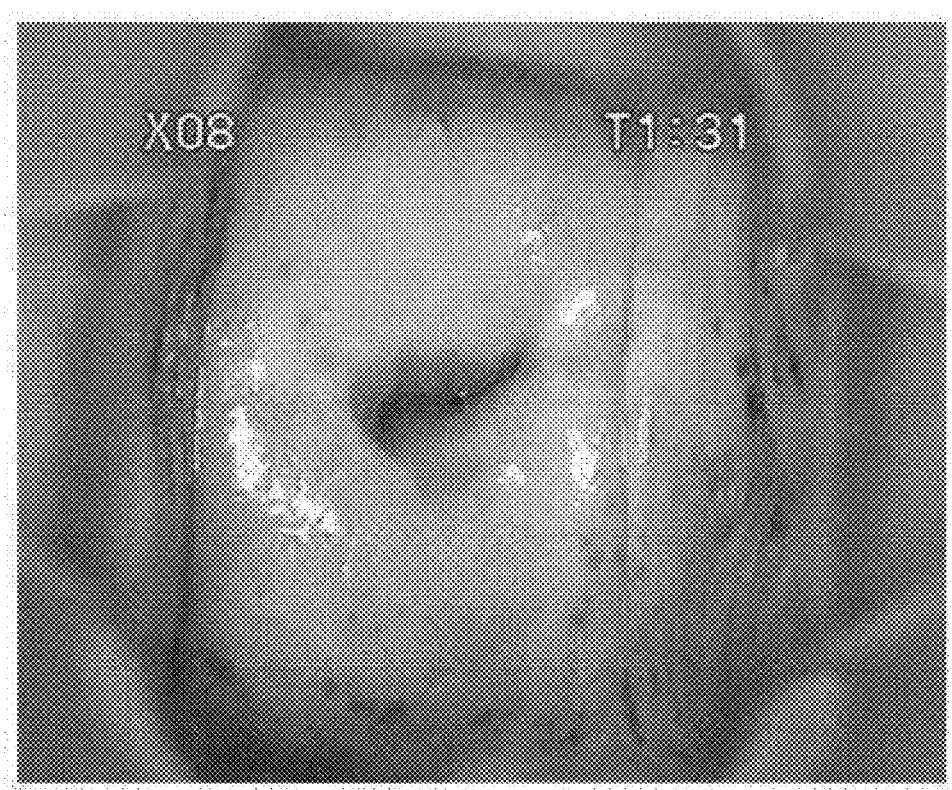
FIG. 7 is an acetic acid state sub-diagram formed when the cervix uteri are exposed to acetic acid for 90 seconds according to the present invention.
Figure 8:
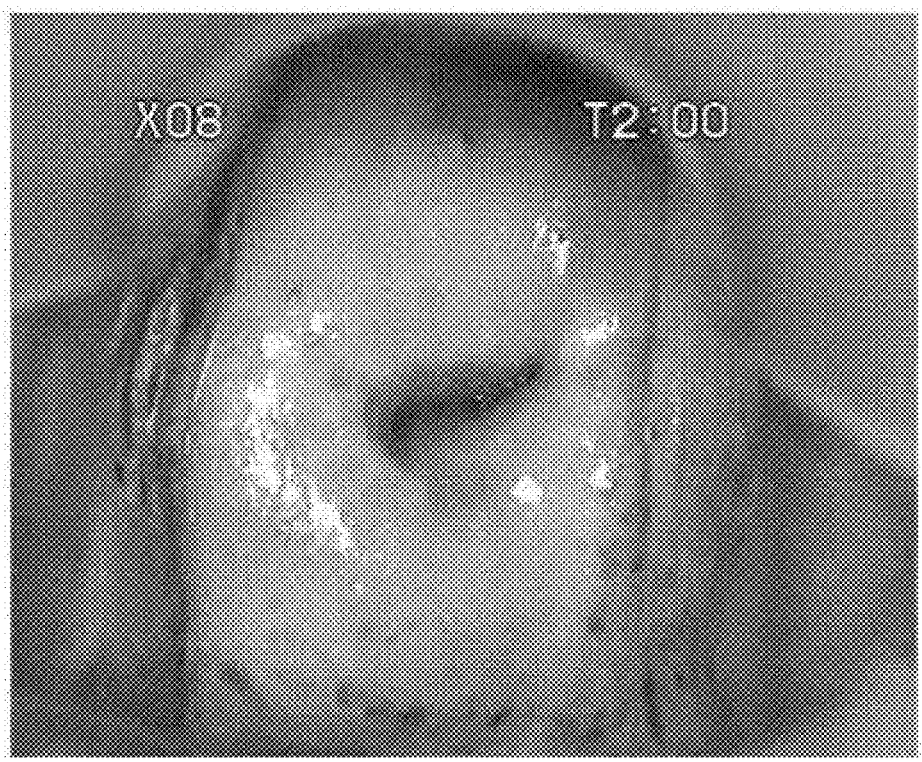
FIG. 8 is a secondary acetic acid state diagram formed when the cervix uteri are exposed to acetic acid for 120 seconds according to the present invention.
Figure 9:
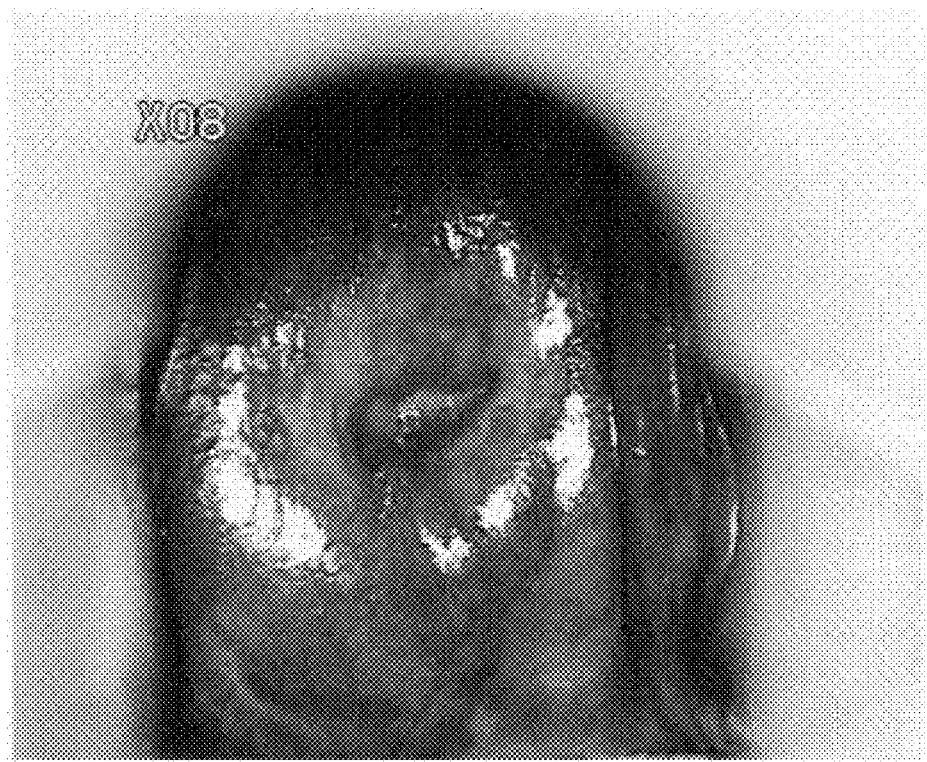
FIG. 9 is an iodine-stained state diagram formed when the cervix uteri are stained with iodine according to the present invention.

With continued reference to FIG. 3, the present invention further provides a method for processing the intelligent assistant judgment system for images of cervix uteri, including:

a step A1 of searching, analyzing and comparing images of cervix uteri to be detected and a preliminary screening model based on the images of the cervix uteri to be detected and characteristic data of the images of the cervix uteri to be detected so as to determine characteristic models which are similar to the images of the cervix uteri to be detected; and a step A2 of comparing image characteristic data of the images of the cervix uteri to be detected with characteristic sub-models to obtain the characteristic sub-models corresponding to the images of the cervix uteri to be detected, A plurality of different preliminary screening case models which consist of images of diseased cervical uteri and a plurality of different preliminary screening normal models which consist of images of normal cervical uteri are arranged in the preliminary screening model, and the characteristic models correspond to the preliminary screening case models. The characteristic models consist of a plurality of different diseased characteristic sub-models, and the characteristic sub-models include lesions type names corresponding to the characteristic sub-models, characteristic parameters of lesion areas, and characteristic images of the lesion areas.

In another embodiment of the present invention, the step A2 in the present invention includes the following steps in detail:

a step A21 of searching, analyzing and comparing the images of the cervix uteri to be detected and the preliminary screening model to determine preliminary screening case models which are similar to the images of the cervix uteri to be detected; and a step A22 of acquiring characteristic models corresponding to the images of the cervix uteri to be detected based on the correspondence between the preliminary screening case models and the characteristic models.

When used, the colposcope device is used for acquiring the images of the cervix uteri to be detected and its characteristic data, and then sending them to the assistant judgment device.

The assistant judgment device reads preliminary screening model data from the storage module through the processing unit, and controls the comparison and analysis module to carry out image pixel comparison and analysis on the images of the cervix uteri to be detected and the primary screening models to determine whether the images of the cervix uteri to be detected belong to the preliminary screening normal model or the preliminary screening case model; if the cervix uteri to be detected belong to the preliminary screening normal model, the processing module shows that the cervix uteri to be detected are in a normal state, thereby realizing the purpose of the preliminary screening.

If the comparison and analysis module analyzes the image to obtain a result that the current cervix uteri to be detected correspond to a certain primary screening case models in the primary screening models, it shows that such cervix uteri to be detected are diseased cervix uteri. At this moment, in order to further determine detailed information of the cervix uteri, the comparison and analysis module of the present invention also compares and analyzes the cervix uteri and the corresponding characteristic models to obtain characteristic sub-models which are similar to the detected cervix uteri so as to determine the information of the diseased cervix uteri and assist the doctors in making the judgment.

The present invention provides an intelligent assistant judgment system for images of cervix uteri. By combining the colposcope device and the assistant judgment device together to obtain the images of the cervix uteri to be detected and its characteristic data by the colposcope device and to compare and analyze the images of the cervix uteri to be detected and its characteristic data by the assistant judgment device, the present invention can judge whether the current cervix uteri to be detected are normal cervix uteri, and can obtain, from the characteristic data of the images of the cervix uteri to be detected, the type of a lesion occurring in the current cervix uteri to be detected and characteristic parameters of the lesion. The doctors are assisted in making correct diagnosis and judgment. This improves the diagnostic level of the doctors and reduces the probability of misdiagnosis and missed diagnosis.

Finally, the method in the present application is only a preferred embodiment, but not used for limiting the scope of the present invention. Any modification, equivalent replacement, improvement, etc. made according to the spirit and principle of the present invention shall fall into the protection scope of the present invention.

What is claimed is:

1. An intelligent assistant judgment system for images of cervix uteri, comprising:

a colposcope device used for acquiring images of cervix uteri to be detected and collecting characteristic data of the images of the cervix uteri to be detected; and an assistant judgment device communicated with the colposcope device, the assistant judgment device comprising a processing unit and a storage module, the storage module being electrically connected to the processing unit, wherein the storage module is provided with a preliminary screening model and a plurality of characteristic models therein, wherein a plurality of different preliminary screening case models which consist of images of diseased cervical uteri and a plurality of different preliminary screening normal models which consist of images of normal cervical uteri are arranged in the preliminary screening model, and the characteristic models correspond to the preliminary screening case models; and the characteristic models consist of a plurality of different diseased characteristic sub-models which comprise lesions type names corresponding to the characteristic sub-models, characteristic parameters of lesion areas, and characteristic images of the lesion areas, wherein the assistant judgment device is configured to analyze the images of cervix uteri to be detected and the preliminary screening model based on the images of the cervix uteri to be detected and the characteristic data of the images of the cervix uteri to be detected so as to determine the characteristic models which are similar to the images of the cervix uteri to be detected, and wherein the assistant judgment device is further configured to compare the image characteristic data of the images of the cervix uteri to be detected with the characteristic sub-models to obtain the characteristic sub-models corresponding to the images of the cervix uteri to be detected.

2. The intelligent assistant judgment system for images of cervix uteri according to claim 1, wherein the assistant judgment device is configured to carry out pixel comparison and analysis on the images of the cervix uteri to be detected and the preliminary screening model in the storage module to obtain the preliminary screening case models corresponding to the images of the cervix uteri to be detected; and the assistant judgment device is configured to carry out pixel comparison and analysis on the images of the cervix uteri to be detected and the characteristic models to find characteristic sub-models which are similar to image data of the cervix uteri to be detected.

3. The intelligent assistant judgment system for images of cervix uteri according to claim 1, wherein the assistant judgment device further comprises a display unit electrically connected to the processing unit.

4. The intelligent assistant judgment system for images of cervix uteri according to claim 1, wherein the images of the cervix uteri comprise six state diagrams, including a white light state diagram formed when the cervix uteri are exposed to white light, a green light state diagram formed when the cervix uteri are exposed to green light, an acetic acid state diagram formed when the cervix uteri are exposed to acetic acid for 60 seconds, an acetic acid state sub-diagram formed when the cervix uteri are exposed to acetic acid for 90 seconds, a secondary acetic acid state diagram formed when the cervix uteri are exposed to acetic acid for 120 seconds and an iodine-stained state diagram formed when the cervix uteri are stained with iodine.

5. The intelligent assistant judgment system for images of cervix uteri according to claim 4, wherein each of the preliminary screening case models and each of the preliminary screening normal models consist of images of the cervix uteri in the six different states, and the characteristic images of the lesion areas in the characteristic sub-models comprise six different state images.

6. The intelligent assistant judgment system for images of cervix uteri according to claim 1, wherein the colposcope device comprises a main colposcope, a controller, an imaging probe, a lighting source and an imaging camera; the lighting source, the controller and the imaging camera are mounted on the main colposcope, and the imaging probe and the lighting source are electrically connected to the controller.

7. A method for processing images of cervix uteri in an intelligent assistant judgment system, comprising:
  using a colposcope to acquire images of the cervix uteri to be detected;
  using a processing unit, a step A1 of analyzing the images of cervix uteri to be detected and a preliminary screening model based on the images of the cervix uteri to be detected and characteristic data of the images of the cervix uteri to be detected so as to determine characteristic models which are similar to the images of the cervix uteri to be detected; and
  using the processing unit, a step A2 of comparing the image characteristic data of the images of the cervix uteri to be detected with characteristic sub-models to obtain the characteristic sub-models corresponding to the images of the cervix uteri to be detected,
  wherein a plurality of different preliminary screening case models which consist of images of diseased cervical uteri and a plurality of different preliminary screening normal models which consist of images of normal cervical uteri are arranged in the preliminary screening model, and the characteristic models correspond to the preliminary screening case models; and the characteristic models consist of a plurality of different diseased characteristic sub-models, and the characteristic sub-models comprise lesions type names corresponding to the characteristic sub-models, characteristic parameters of lesion areas, and characteristic images of the lesion areas.

8. The method for processing images of cervix uteri according to claim 7, wherein the step A2 comprises:
  a step A21 of analyzing, based on the assistant judgment system, the images of the cervix uteri to be detected and the preliminary screening model to determine preliminary screening case models which are similar to the images of the cervix uteri to be detected; and
  a step A22 of acquiring characteristic models corresponding to the images of the cervix uteri to be detected based on the correspondence between the preliminary screening case models and the characteristic models.

* * * * *